United States Patent
Egnelöv et al.

(10) Patent No.: US 7,094,209 B2
(45) Date of Patent: Aug. 22, 2006

(54) METHOD FOR INTRODUCER REPLACEMENT

(75) Inventors: Per Egnelöv, Uppsala (SE); Fredrik Preinitz, Uppsala (SE); Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 313 days.

(21) Appl. No.: 10/341,598

(22) Filed: Jan. 14, 2003

(65) Prior Publication Data

US 2004/0138589 A1    Jul. 15, 2004

(51) Int. Cl.
*A61B 5/00* (2006.01)
*A61M 25/00* (2006.01)

(52) U.S. Cl. .................. 600/585; 600/433; 600/434; 600/435; 604/164.13

(58) Field of Classification Search ............... 600/585; 604/264, 523, 528; 606/213
See application file for complete search history.

(56) References Cited

U.S. PATENT DOCUMENTS

| 4,925,445 | A | * | 5/1990 | Sakamoto et al. | .......... 604/528 |
| 5,007,902 | A |   | 4/1991 | Witt | |
| 5,120,323 | A | * | 6/1992 | Shockey et al. | ............ 604/528 |
| 5,281,203 | A | * | 1/1994 | Ressemann | ............ 604/164.13 |
| 5,417,669 | A | * | 5/1995 | Castaneda et al. | .......... 604/264 |
| 5,431,639 | A |   | 7/1995 | Shaw | |
| 5,441,504 | A | * | 8/1995 | Pohndorf et al. | ............ 606/129 |
| 5,478,326 | A |   | 12/1995 | Shiu | |
| 5,558,635 | A | * | 9/1996 | Cannon | ...................... 604/500 |
| 5,658,262 | A | * | 8/1997 | Castaneda et al. | .......... 604/264 |
| 5,676,689 | A |   | 10/1997 | Kensey et al. | |
| 5,695,111 | A |   | 12/1997 | Nanis et al. | |
| 5,749,370 | A | * | 5/1998 | Brooks et al. | .............. 600/585 |
| 5,855,559 | A |   | 1/1999 | Van Tassel et al. | |
| 6,090,130 | A |   | 7/2000 | Nash et al. | |
| 6,245,054 | B1 | * | 6/2001 | Fuimaono et al. | .......... 604/523 |
| 6,623,509 | B1 | * | 9/2003 | Ginn | ......................... 606/213 |
| 2003/0088195 | A1 | * | 5/2003 | Vardi et al. | ................. 600/585 |
| 2003/0195560 | A1 |   | 10/2003 | Ginn | |

FOREIGN PATENT DOCUMENTS

| DE | 43 19 033 C1 | 6/1994 |
| EP | 0 331 932 A2 | 9/1989 |
| EP | 0 397 173 A1 | 11/1990 |

\* cited by examiner

*Primary Examiner*—Max Hindenburg
*Assistant Examiner*—Rene Towa
(74) *Attorney, Agent, or Firm*—Foley & Lardner LLP

(57) ABSTRACT

The invention provides a method for replacing a first introducer, whose distal end is inside a vessel and whose proximal end is outside the skin of a patient, with a second introducer. The method comprises the steps of inserting a guide rod into the first introducer, removing the first introducer, passing the second introducer over the guide rod, and removing the guide rod. The guide rod to be used according to the method has preferably a flexible distal portion with a blunt distal end and a stiff proximal portion with a tapered proximal end.

9 Claims, 3 Drawing Sheets

METHOD FOR INTRODUCER REPLACEMENT

FIELD OF THE INVENTION

The present invention relates generally to a method for replacing an introducer, which is inserted in a vessel, with another introducer, and more particularly to a method for replacing an introducer with another introducer without the conventional use of a guide wire and a dilator.

BACKGROUND OF THE INVENTION

In U.S. Pat. No. 6,090,130, which is assigned to Kensey Nash Corporation, a system for sealing a percutaneous puncture in a blood vessel is disclosed. For the determination of the position of the blood vessel, the system comprises a blood vessel locator, which, in turn, comprises an introducer sheath and a dilator. The position of the blood vessel is determined by observing a flow of blood out from a hole in the proximal end of the introducer sheath. The hole in the proximal end of the introducer sheath is via a canal in fluid communication with a hole in the distal end of the vessel locator. U.S. Pat. No. 6,090,130 discloses several different embodiments of how this canal and the distal hole can be arranged. A common requirement for these embodiments is, however, that the length of the dilator is adapted to the length of the introducer sheath.

U.S. Pat. No. 6,090,130 describes also a typical, conventional, intravascular surgical procedure, in which an introducer sheath according to the patent can be used. It is said that in such a procedure, a cannula of an instrument, such as an angiographic needle, is inserted percutaneously through the skin into the artery, such as the femoral artery, at the situs for the instrument's insertion. The needle cannula is held in place and the flexible end of a mini-guidewire is then passed through the cannula into the artery to the desired length. Once the mini-guide is in place, the needle cannula is removed, leaving the guidewire in place. An introducer sheath and an arterial dilator are then passed over the guidewire, through the puncture or incision and into the artery. The guidewire and then the dilator are removed, leaving the introducer sheath in place. A catheter, or other intravascular instrument, is then inserted through the introducer sheath and threaded down the artery to the desired intravascular location.

In the above description of the intravascular surgical procedure, which is taken directly from U.S. Pat. No. 6,090,130 and which is based on the so-called Seldinger technique, it is explicitly assumed (by reference numerals) that the introducer sheath being used during the intravascular procedure is the same introducer sheath as the introducer sheath into which a dilator is inserted when the intravascular operation has been completed and the sealing operation is to be performed. In other words, it is assumed that there is only one introducer sheath used during the whole medical operation, i.e. during both the actual intravascular procedure and the subsequent sealing operation. Although this could be the case, it is to the best of the present applicants' knowledge almost never actually the case. The reason for this is mainly that the needle cannula, introducer sheath, dilator, guide wire and catheter, and possibly some more instruments, come together in a separate set, which presumably is provided by another company than the company that provides the sealing system, i.e. in this particular example the Kensey Nash Corporation. Now, if the length of the special dilator, which is used to provide the canal in the vessel locator according to U.S. Pat. No. 6,090,130, does not match the length of the introducer sheath which already is inserted in the artery, this introducer sheath has to be replaced with an introducer sheath having the suitable, known length. Since introducer sheaths come in a variety of dimensions, the first introducer, which is inserted in the artery, must usually be replaced, and a special replacement technique has been developed for this purpose. In one stage, this known replacement technique requires that a medically trained person apply manual compression pressure, and the technique requires further that two separate instruments, a guide wire and a dilator, are used.

SUMMARY OF THE INVENTION

An object of the present invention is therefore to provide an improved method for replacing a first introducer, whose distal end is inserted into a vessel and whose proximal end is outside the skin (or other tissue) of a patient, by a second introducer.

Another object of the invention is to provide a guide rod, which is used in the method according to the invention and which replaces the guide wire and the dilator used in the previously known replacement method.

In the method according to the invention, a guide rod is first inserted into the first introducer, which is in place in the vessel. The first introducer is then removed, thereby leaving only the guide rod in place. Thereafter, the second introducer is passed over the guide rod and into the vessel, and in a last step the guide rod is removed.

To not damage the vessel, the guide rod according to the invention should preferably have a flexible distal portion with a blunt distal end, while the proximal portion, which has a tapered proximal end, should be stiffer to facilitate the threading of the second introducer.

DETAILED DESCRIPTION OF THE PREFERRED EMBODIMENTS

Before describing the method according to the present invention, a brief description of the method previously utilized to replace a first introducer, whose distal end is inside a vessel and whose proximal end extends out of the skin of a patient, with a second introducer, will be provided. This well-known method may be used, as mentioned above, to replace the first introducer with a second introducer having a length that matches the length of a dilator, which is designed in such a way that the combination of the dilator and the second introducer can be used as a vessel locator. The method could, however, be used whenever one wants to change introducer, for instance when a new introducer having a larger diameter is needed.

Figure 1:
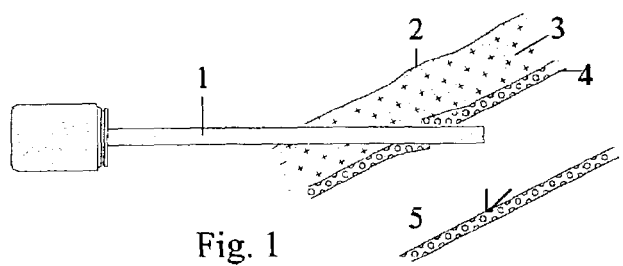
FIGS. 1–5 illustrate the steps in a replacement procedure according to the prior art.

FIG. 1 illustrates a situation in which a first introducer 1 has been inserted through a puncture hole, which extends from the skin 2 of a patient, through tissue 3 and through the wall 4 of a blood vessel 5, such that the distal end of the introducer 1 is inside the blood vessel 5 while the proximal end of the introducer 1 is outside the skin 2. The situation illustrated in FIG. 1 represents a starting point for the conventional method to be described below in conjunction with FIG. 2 to FIG. 5.

Figure 2:
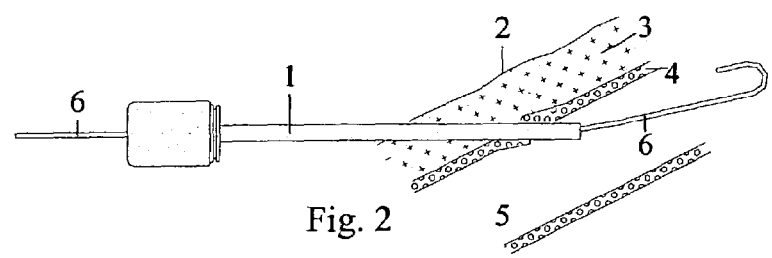

In FIG. 2, the first step of the conventional method is shown. In this first step, a guide wire 6 is introduced into the introducer 1 until the distal end of the guide wire 6 is well inside the blood vessel 5.

Figure 3:
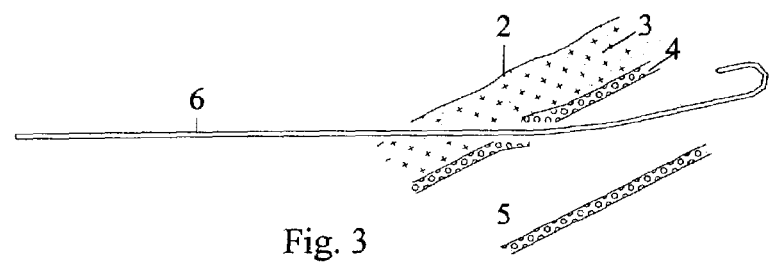

The second step of the conventional method involves the removal of the introducer 1, thereby leaving only the guide wire 6 in place, as is illustrated in FIG. 3. Here, the basic disadvantage of the conventional method is apparent. The diameter of the guide wire 6 is much less than the diameter of the puncture hole, and in particular less than the diameter of the hole in the wall 4 of the blood vessel 5, which means that blood can flow out from the blood vessel 5. At this stage, external manual compression pressure is usually applied (not shown) in order to reduce the flow of blood out from the blood vessel 5. Besides the problem that it can be difficult to apply enough compression pressure to completely prevent bleeding from the blood vessel 5, some blood will always flow out from the blood vessel 5. The reason for this is that the compression pressure cannot be applied during the insertion of a second introducer, since compression of the tissue 3 and the vessel 5 would apparently prevent this insertion.

Figure 4:
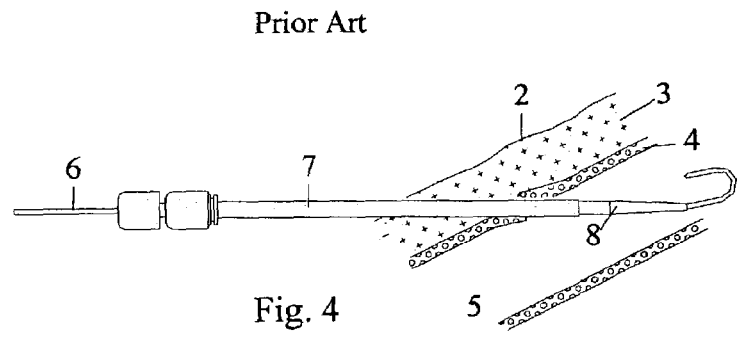
Figure 5:
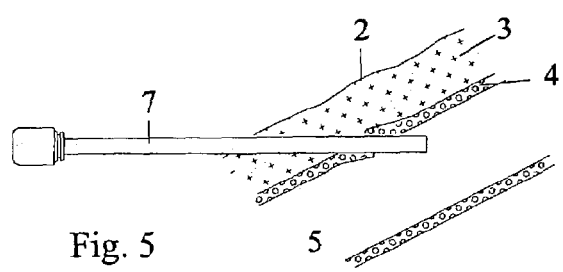

FIG. 4 shows the third step of the conventional method, in which a second introducer 7 and a dilator 8 are passed over the guide wire 6 until the distal end of the introducer 7 is inside the blood vessel 5. In subsequent steps (not shown), first the guide wire 6 and then the dilator 8 are removed, thereby leaving only the second introducer 7 in place, as is illustrated in FIG. 5. Here it should be noted that to accomplish the substitution illustrated in FIG. 1 to FIG. 5, both the guide wire 6 as well as the dilator 8 are needed. It can also be mentioned that the removal of the introducer 1, the application of the manual compression and the insertion of the second introducer 7, with the dilator 8 inserted therein, sometimes can be accomplished by a single skilful doctor, but often a second medically trained person is required.

Figure 6:
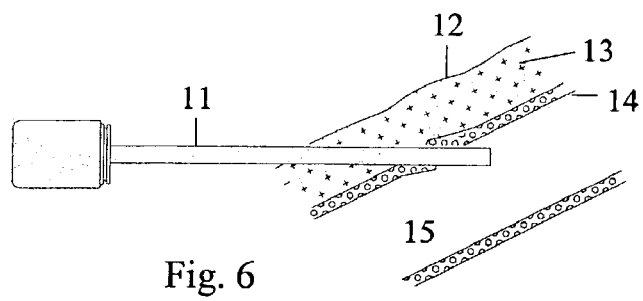
FIGS. 6–10 illustrate the steps in a replacement procedure according to the present invention.

The replacement method according to the present invention is now going to be described. Like the conventional method described in conjunction with FIG. 1 to FIG. 5, the present replacement method could be used whenever one wants to replace a first introducer with a second introducer. The starting point of the present method is the same as for the conventional method, and in FIG. 6 is illustrated a situation in which a first introducer 11 has been inserted through a puncture hole, which extends from the skin 12 of a patient, through tissue 13 and through the wall 14 of a blood vessel 15, such that the distal end of the introducer 11 is inside the blood vessel 15 while the proximal end of the introducer 11 is outside the skin 12.

Figure 7:
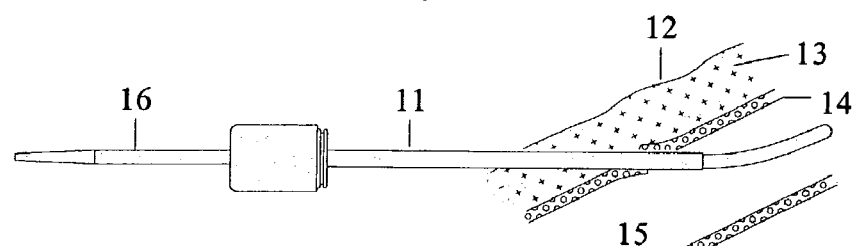

In FIG. 7, the first step of the present method is shown. In this first step, a guide rod 16 is introduced into the introducer 11 until the distal end of the guide rod 16 is well inside the blood vessel 15.

Figure 8:
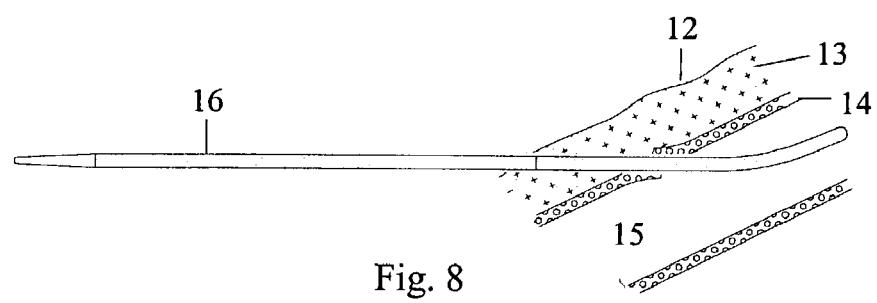

The second step of the present method involves the removal of the introducer 11, thereby leaving only the guide rod 16 in place, as is illustrated in FIG. 8. Here, one advantage of the present method is apparent. The diameter of the guide rod 16 is equal to the inner diameter of the introducer 11, and, more importantly, the diameter of the guide rod 16 is equal, or almost equal, to the diameter of the puncture hole in the wall 14 of the blood vessel 15. Furthermore, when the introducer 11 is removed, the hole in the vessel wall 14 contracts slightly around the guide rod 16, which means that there will be essentially no flow of blood out from the blood vessel 15. This is an advantage in itself; and since no external manual compression pressure has to be applied, one manual operation less has to be executed. One operation less may sound insignificant, but could actually imply that one medically trained person is saved for other duties, or if only one doctor is carrying out the operation, that he or she can concentrate on the insertion of the second introducer.

Figure 9:
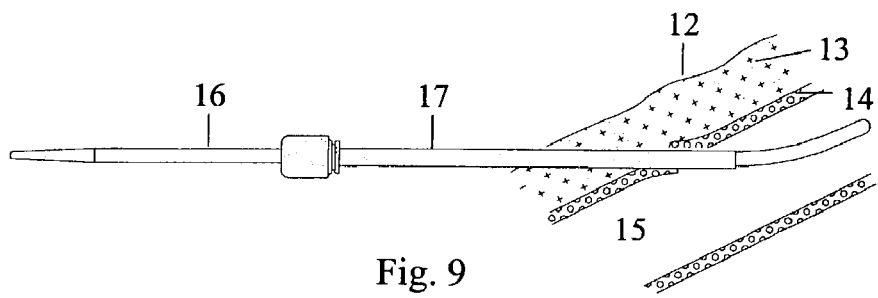
Figure 10:
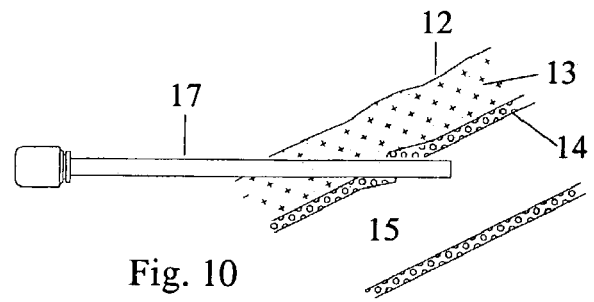

FIG. 9 shows the third step of the present method, in which a second introducer 17 is passed over the guide rod 16 until the distal end of the introducer 17 is inside the blood vessel 15. In a subsequent step (not shown), the guide rod 16 is removed, thereby leaving only the second introducer 17 in place, as is illustrated in FIG. 10. Here it should be noted that to accomplish the substitution illustrated in FIG. 6 to FIG. 10, only one instrument, i.e. the guide rod 16, is needed, which is in contrast to the conventional method in which two instruments, i.e. the guide wire and the dilator, were needed.

Figure 11:
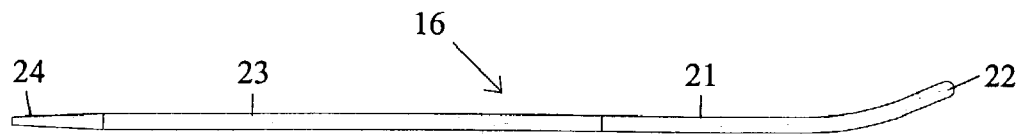
FIG. 11 shows the guide rod used in the replacement procedure according to the present invention.

The guide rod 16 used in the present method described above is illustrated separately in FIG. 11. The guide rod 16 has a distal portion 21 with a distal end 22 and a proximal portion 23 with a proximal end 24. The distal portion 21 should preferably be flexible, so that the risk of damaging a vessel during insertion is minimized. To further reduce this risk, the distal end 22 should preferably be blunt. Further, the distal portion 21 should preferably be made from a material that can be pre-bent in such a way that the distal portion 21, after its passage through an introducer, resumes its bent shape. The bent shape, which also is common for a conventional guide wire, facilitates the insertion of the guide rod 16 into a vessel. To facilitate the threading of an introducer over the guide rod 16, the proximal portion 23 should preferably be stiff and the proximal end 24 of the proximal portion 23 should preferably be tapered. With a stiff proximal portion 23 having a tapered end 24 it is considerably easier to thread an introducer over the guide rod 16, as is done in the method according to the present invention, than to thread a dilator over a guide wire, as is done in the conventional method. The guide rod 16 could be made from any suitable materials, such as plastic or metal, and the distal portion could, for example, be made in the form of a coil spring. In the FIG. 11 embodiment, the guide rod 16 has an outer diameter of 3 French (1 mm) or greater, such as 6 French, 7 French, 8 French, or more.

Figure 12:
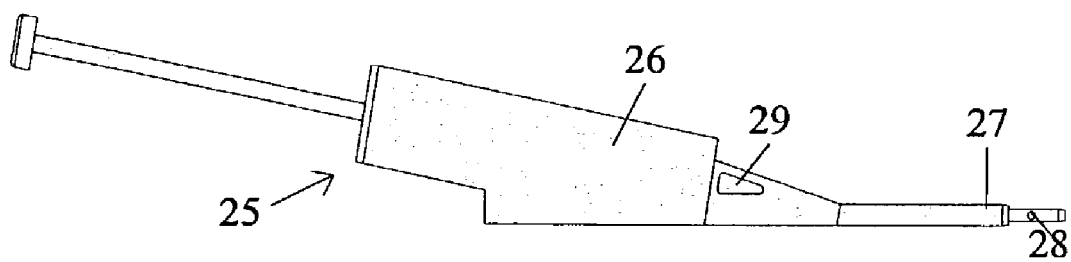
FIGS. 12 and 13 show the design and use of a tool for closing a puncture wound.

Above, the second introducer, such as the introducer 17 illustrated in FIG. 10, has been described as a separate item, to which a tool for sealing a percutaneous puncture may be connected, as, for example, is described in the above-mentioned U.S. Pat. No. 6,090,130. It should, however, be understood that the method and the guide rod according to the present invention equally well can be used in a situation where the second introducer is an integrated part of a tool for closing a puncture wound. The term "introducer" is therefore herein meant to encompass both separate introducers and introducers which are part of another device. In FIG. 12 such a tool 25 for closing a puncture wound is illustrated. The tool 25 comprises basically a housing 26 and a distal introducer 27, which is fixedly connected to the housing 26. The introducer 27 is provided with a first hole 28, which through a canal (not shown in the figure) is in fluid communication with an opening 29 provided in the housing 26. This canal can be provided as a longitudinal recess in the surface of a guide rod over which the introducer 27 is threaded, or the canal can be provided as a longitudinal, internal hole within the guide rod.

Figure 13:
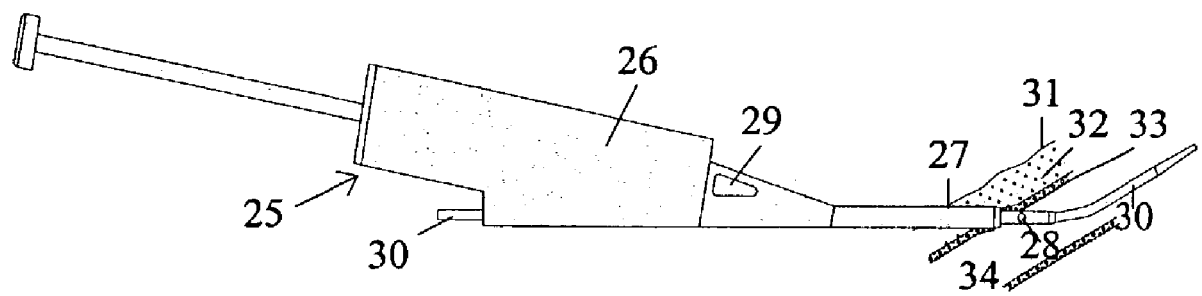

In FIG. 13, the introducer 27 of the tool 25 has, over a guide rod 30, been inserted from the skin 31 of a patient, through tissue 32 and through the wall 33 of a blood vessel 34. The introducer 27 is positioned by means of the same positioning operation as was illustrated in FIG. 7 to FIG. 9, and the introducer 27 of FIG. 13 is therefore in the same position as the introducer 17 of FIG. 9, with the difference that the introducer 27 is a part of a tool 25 for closing a puncture wound rather than being a separate introducer. In the position shown in FIG. 13, blood can flow into the hole 28 in the introducer 27 through a canal provided in the guide rod and out from the opening 29 provided in the housing 26, thereby providing a user with a verification that the introducer 27 is at the correct position with the vessel 34.

Although the present invention has been described with reference to specific embodiments, also shown in the appended drawings, it will be apparent for those skilled in the art that many variations and modifications can be done within the scope of the invention as described in the specification and defined with reference to the following claims. It should, for example, be clear that the method and the guide rod according to the present invention are not limited to be used in blood vessels, but could be used in any vessel when a first introducer has to be replaced with a second introducer. As another example, the guide rod could be provided with a measurement scale, for example, in the form of centimeter or millimeter marks, that provide a user with an indication of how far the guide rod is inserted into the introducer.

What is claimed is:

1. A method for replacing a first introducer, whose distal end is inside a vessel and whose proximal end is outside the skin of a patient, with a second introducer, said method comprising the steps of:
    inserting a guide rod into the first introducer until the distal end of the guide rod is inside the vessel,
    removing the first introducer, thereby leaving only the guide rod in place such that the guide rod plugs a hole in the vessel such that there is substantially no flow of blood out from the vessel,
    passing the second introducer over the guide rod until the distal end of the second introducer is inside the vessel, and
    removing the guide rod, thereby leaving only the second introducer in place.

2. The method according to claim 1, wherein the guide rod is solid.

3. The method according to claim 2, wherein a distal portion of the guide rod has a blunt end.

4. The method according to claim 2, wherein a proximal portion of the guide rod has a tapered end.

5. The method according to claim 2, wherein a distal portion of the guide rod can be pre-bent in such a way that it resumes its bent shape after having passed through the first introducer.

6. The method according to claim 2, wherein a diameter of the guide rod is approximately the same size as the hole in a wall of the vessel.

7. The method according to claim 2, wherein the guide rod further comprises a measurement scale.

8. The method according to claim 2, wherein the guide rod comprises a flexible distal portion and a stiff proximal portion.

9. A method for replacing a first introducer, whose distal end is inside a vessel and whose proximal end is outside the skin of a patient, with a second introducer, said method comprising the steps of:
    inserting a guide rod into the first introducer until the distal end of the guide rod is inside the vessel,
    removing the first introducer, thereby leaving the guide rod in place such that the guide rod plugs a hole in the vessel such that there is substantially no flow of blood out from the vessel,
    passing the second introducer over the guide rod until the distal end of the second introducer is inside the vessel, and
    removing the guide rod, thereby leaving the second introducer in place.

* * * * *